United States Patent [19]

Friebe et al.

[11] 4,348,401

[45] Sep. 7, 1982

[54] N-PHENOXYALKYLPIPERIDINE DERIVATIVES

[75] Inventors: Walter-Gunar Friebe, Darmstadt; Wolfgang Kampe, Heddesheim; Max Thiel, Mannheim; Wolfgang Schaumann, Heidelberg; Otto-Henning Wilhelms, Weinheim-Rittenweier, all of Fed. Rep. of Germany

[73] Assignee: Boehringer Mannheim GmbH, Mannheim, Fed. Rep. of Germany

[21] Appl. No.: 185,839

[22] Filed: Sep. 10, 1980

[30] Foreign Application Priority Data

Sep. 28, 1979 [DE] Fed. Rep. of Germany ....... 2939292

[51] Int. Cl.³ .............. A61K 31/445; A61K 31/455; C07D 211/58; C07D 409/12; C07D 407/12; C07D 403/12

[52] U.S. Cl. .................................... 424/267; 424/264; 546/210; 546/194; 546/223; 546/224; 546/230; 546/233; 546/234

[58] Field of Search .............. 546/210, 224, 223, 230, 546/194; 424/267, 264

[56] References Cited

U.S. PATENT DOCUMENTS 3,255,196  6/1966  Debarre et al. ..................... 546/230
4,027,028  5/1977  Vincent et al. ..................... 546/224

Primary Examiner—Norma S. Milestone
Attorney, Agent, or Firm—Sprung, Horn, Kramer & Woods

[57] ABSTRACT

An N-phenoxyalkylpiperidine derivative of the formula

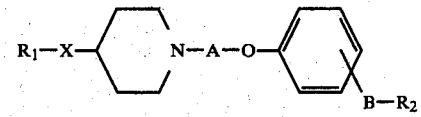

wherein $R_1$ is a hydrogen atom, an acyl radical or an optionally substituted aryl radical, $R_2$ is a hydroxymethyl radical, a cyano group, an amidino group, an amidino group substituted by hydroxyl, a 1H tetrazol-5-yl radical or a —CO—$R_3$ radical, $R_3$ is a hydroxyl group, a lower alkoxy radical, an amino group, or an amino group substituted by a 1H-tetrazol-5-yl radical, X is an imino group or an oxymethyl radical, A is an alkylene radical containing 2 to 4 carbon atoms, and B is a valency bond or a 4-hydroxypyrimidin-2,5-diyl radical; or a pharmacologically acceptable salt thereof. The compounds exhibit anti-histaminic, anti-oedematous and anti-phlogistic activity.

6 Claims, No Drawings

N-PHENOXYALKYLPIPERIDINE DERIVATIVES

The present invention is concerned with new N-phenoxyalkylpiperidine derivatives, with the preparation thereof and with pharmaceutical compositions containing them.

The new piperidine derivatives according to the present invention are compounds of the general formula:

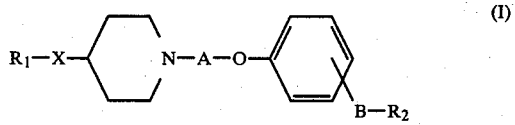

wherein $R_1$ is a hydrogen atom, an acyl radical or an optionally substituted aryl radical, $R_2$ is a hydroxymethyl radical, a cyano group, an amidino group which is optionally substituted by hydroxyl, a 1—H-tetrazol-5-yl radical or a —CO-$R_3$ radical, $R_3$ is a hydroxyl group, a lower alkoxy radical or an amino group which is optionally substituted by a 1H-tetrazol-1-yl radical, X is an imino group or an oxymethyl radical, A is an alkylene radical containing 2 to 4 carbon atoms and B is a valency bond or a 4-hydroxypyrimidin-2,5-diyl radical; and the pharmacologically acceptable salts thereof with non-toxic organic and inorganic acids and bases.

The new compounds according to the present invention have an anti-allergic action, especially due to their strongly anti-histaminic action, which can be demonstrated on the skin and bronchial system. Furthermore, an anti-oedematous and anti-phlogistic effectiveness is clearly marked.

Published Federal Republic of Germany Pat. No. 27 37 630 describes heterocyclic oxyalkylpiperidines with a phenoxymethyl radical in the 4-position but these compounds possess β-blocking properties.

The acyl radicals of the substituent $R_1$ can be lower alkanoyl radicals, which are optionally substituted by halogen or aryl, or are carbocyclic or heterocyclic aroyl radicals, which can be substituted by halogen, hydroxyl, lower alkyl, lower alkoxy, lower alkoxycarbonyl, lower acyloxy, carboxyl, nitro, amino, nitrile, trifluoromethyl, carbamoyl, lower alkylthio, lower alkylsulphinyl, lower alkylsulphonyl, lower alkanoyl, aroyl, acylamino, hydroxy lower alkyl or lower alkoxy lower alkyl. The lower alkyl radicals in the mentioned radicals contain up to 6 and preferably up to 4 carbon atoms, the radicals being straight-chained or branched.

Heterocyclic aroyl radicals can be, for example, the furane-carbonyl, thiophene-carbonyl or pyridine-carbonyl radical and the carbocyclic aroyl radical can be, for example, the benzoyl radical.

Furthermore, $R_1$ can be an acid residue derived from a cycloalkylcarboxylic acid, cycloalkyl thereby preferably being a cyclopropyl, cyclobutyl, cyclopentyl, cyclohexyl or cycloheptyl radical.

In addition, when $R_1$ is an acyl radical, it can also be an acid residue derived from a sulphonic acid, for example, benzenesulphonic acid or methanesulphonic acid. The term "aryl" in the definition of the substituent $R_1$ preferably means a phenyl or naphthyl radical. Aryl substituents which may, if desired, be present, include hydroxyl, halogen, lower alkyl or lower alkoxy radicals containing up to 6 carbon atoms.

The halogen atoms are to be understood to be fluorine, chlorine and bromine atoms.

The alkylene radical represented by A can be straight-chained or branched, the trimethylene radical being preferred.

Apart from the compounds mentioned hereinafter in the examples, the present invention also includes, in particular, all compounds which have every possible combination of the substituents mentioned in the examples.

The present invention also includes compounds of general formula (I), in which $R_1$, X and A have the above-given meanings, B is a valency bond and $R_2$ is a cyano group, as intermediates for the preparation of analogous compounds in which $R_2$ is a 1H-tetrazol-5-yl radical.

The present invention also provides a process for the preparation of compounds of general formula (I), wherein a compound of the general formula:

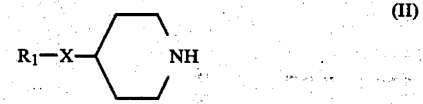

in which $R_1$ and X have the same meanings as above, is reacted with a compound of the general formula:

in which $Y_1$ and $Y_2$ are reactive residues and A has the same meaning as above, and with a compound of the general formula:

in which B and $R_2$ have the same meanings as above, whereafter, if desired, the substituent $R_1$ or the radical —B—$R_2$ is converted in known manner into another substituent $R_1$ or into a radical —B—$R_2$ as defined above, and the reaction product obtained is, if desired, converted into a pharmacologically acceptable salt.

The reactive residues $Y_1$ and $Y_2$ in the compounds of general formula (III) can be, for example, chlorine or bromine atoms or mesyloxy or tosyloxy radicals.

The process according to the present invention can be carried out by first condensing a compound of general formula (III) with a compound of general formula (IV) and isolating the intermediate product obtained, whereafter this intermediate product is reacted with a compound of general formula (II). The reaction is preferably carried out in an alkaline medium and preferably in a lower alcohol, for example isopropyl alcohol, in the presence of sodium isopropanolate.

According to another variant of the process according to the present invention, a compound of general formula (II) is first reacted with a compound of general formula (III) and the reaction mixture obtained is subsequently reacted with a compound of general formula (IV) to give the desired end product of general formula (I).

A subsequent conversion of $R_1$ in compounds of general formula (I) into another substituent $R_1$ can be carried out, for example, by acylation of a compound of general formula (I), in which $R_1$ is a hydrogen atom, with a compound of the general formula $R_1-Z$, in which Z is a reactive residue and $R_1$ has the same meaning as above other than hydrogen. Reactive residues Z can be all residues which are used in peptide chemistry for the activation of carboxylic acids, for example, halogen atoms, the azido group and alkyloxy, aryloxy and acyloxy radicals. A subsequent conversion of the radical $-B-R_2$ can be carried out, for example, by acidic or alkaline hydrolysis of a cyano group to give a carboxyl group or a carboxamido group, by reaction of a cyano group with hydrazoic acid or with a salt thereof to give a 1H-tetrazol-5-yl radical, by the conversion of a cyano group into an amidooxime group, by conversion of an amidooxime group into an amidino group, by esterification of a carboxyl group, by hydrolysis of an ester group, by reduction of an ester group to a hydroxymethyl radical, by amidation of a carboxyl group to a carboxamido group or to a tetrazolylcarboxamido radical or by reaction of an amidino group with an alkoxymethylenemalonic acid ester derivative to give a 5-alkoxycarbonyl-4-hydroxypyrimidin-2-yl radical.

The compounds of general formulae (II), (III) and (IV) are either known from the literature or can be easily prepared from known compounds using well-known methods. Thus, for example, aryloxymethyl-4-piperidines are known from published Federal Republic of Germany Patent No. 25 49 999.

Depending upon the process conditions and the starting materials, possibly salt-forming end materials of general formula (I) are obtained in free form or in the form of their salts which can be converted into one another or into other salts in the usual manner. Thus, for example, acidic end products, such as carboxylic acids and tetrazoles, are obtained in free form or in the form of salts with bases. When free acidic compounds are obtained, they can be converted in the usual way, for example by reaction with appropriate basic agents, into salts with the bases, for example, salts with organic amines or metal salts. Preferred metal salts include, for example, the alkali metal salts and the alkaline earth metal salts, such as the sodium, potassium, magnesium and calcium salts. The free acids can be liberated from the salts in the usual manner, for example by reaction with acidic agents. In the same way, basic compounds are obtained in the free form or in the form of their salts with acids. When salts are obtained with acids, they can be converted in the usual manner into the free compounds, for example with alkalis or ion exchangers. These free compounds can be reacted with organic or inorganic acids and especially with those which are suitable for the formation of therapeutically useful salts. Examples of such acids include hydrohalic acids, sulphuric acid, phosphoric acid, nitric acid, perchloric acid and aliphatic, alicyclic, aromatic and heterocyclic carboxylic and sulphonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phenylacetic acid, benzoic acid, p-aminobenzoic acid, anthranilic acid, p-hydroxybenzoic acid, salicylic acid, p-aminosalicylic acid, embonic acid, methanesulphonic acid, ethanesulphonic acid, hydroxyethanesulphonic acid, ethylenesulphonic acid, halobenzenesulphonic acid, toluenesulphonic acid, naphthalenesulphonic acid and sulphanilic acid, as well as amino acids, such as methionine, tryptophane, lysine and arginine.

These and other salts can also be used for the purification of the new compounds according to the present invention, for example, by converting the free compounds into salts which are isolated and again converted into the free compounds. As a result of the close relationship between the new compounds in their free form and in the form of their salts, in the preceding description and in the following description, references to the free compounds are also to be understood to refer to the corresponding salts.

For the preparation of pharmaceutical compositions, the new compounds according to the present invention are mixed in the usual way with appropriate solid or liquid pharmaceutical carrier substances and aroma, flavoring and coloring materials and formed, for example, into tablets or dragees or, with the addition of appropriate adjuvants, suspended or dissolved in water or an oil, for example olive oil.

The new compounds of general formula (I) and the salts thereof can be administered enterally and parenterally in liquid or solid form. For this purpose, all the usual forms of administration can be used, for example, tablets, capsules, dragees, syrups, solutions, suspensions and the like. As an injection medium, it is preferred to use water which contains the additives usual in the case of injection solutions, such as stabilizing agents, solubilizing agents and buffers. Additives of this kind include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carrier materials for injection solutions must be sterile and are preferably placed into ampules. Solid carrier materials include, for example, starch, lactose, mannitol, methyl cellulose, talc, highly dispersed silicic acids, high molecular weight fatty cids (such as stearic acid), gelatine, agar-agar, calcium phosphate, magnesium stearate, animal and vegetable fats and solid high molecular weight polymers (such as polyethylene glycols). Compositions suitable for oral administration can, if desired, also contain flavoring and/or sweetening materials.

The dosage administered depends upon the age, the state of health and the weight of the recipient, the extent of the disease, the nature of possibly simultaneously carried out further treatments, the frequency of the treatment and the nature of the desired action. The daily dosage of the active compound is normally from 0.1 to 50 mg./kg. of body weight. Generally, 0.5 to 40 and preferably 1.0 to 20 mg./kg., in one or more administrations, are effective for obtaining the desired results.

Besides the compounds mentioned in the following examples, the following compounds are also preferred according to the present invention:
5-{2-[3-(4-trifluoroacetamidopiperidino)-propoxy]-phenyl}-1H-tetrazole
5-{2-{3-[4-(4-methoxycarbonylbenzamido)-piperidino]-propoxy}-phenyl}-1H-tetrazole
5-{2-{3-[4-(4-carboxybenzamido)-piperidino]-propoxy}-phenyl}-1H-tetrazole
5-{2-{3-[4-(4-cyanobenzamido)-piperidino]-propoxy}-phenyl}-1H-tetrazole
5-{2-{3-[4-(3-trifluoromethylbenzamido)-piperidino]-propoxy}-phenyl}-1H-tetrazole
5-{2-{3-[4-(4-aminocarbonylbenzamido)-piperidino]-propoxy}-phenyl}-1H-tetrazole
5-{2-{3-[4-(4-methylthiobenzamido)-piperidino]-propoxy}-phenyl}-1H-tetrazole 5-{2-{3-[4-(4-methylsulphinylbenzamido)-piperidino]-propoxy}-phenyl}-1H-tetrazole 5-{2-{3-[4-(4-methylsulphonylbenzamido)-piperidino]-propoxy}-phenyl}-1H-tetrazole 5-{2-{3-[4-(4-acetylbenzamido)-piperidino]-propoxy}-phenyl}-1H-tetrazole 5-{2-{3-[4-(2-benzoylbenzamido)-piperidino]-propoxy}-phenyl}-1H-tetrazole 5-{2-{3-[4-(2-acetamidobenzamido)-piperidino]-propoxy}-phenyl}-1H-tetrazole 5-{2-{3-[4-(4-hydroxymethylbenzamido)-piperidino]-propoxy}-phenyl}-1H-tetrazole 5-{2-{3-[4-(2-methoxymethylbenzamido)-piperidino]-propoxy}-phenyl}-1H-tetrazole The following examples, which are given for the purpose of illustrating the present invention, describe some of the numerous process variants which can be used for the preparation of the new compounds of general formula (I) according to the present invention:

EXAMPLE 1

2-[3-(4-Phenylacetamidopiperidino)-propoxy]-benzonitrile.

5.35 g. (0.045 mol) 2-Hydroxybenzonitrile are added to a solution of 1.03 g. (0.045 mol) sodium in 100 ml. propan-2-ol. The reaction mixture is heated under reflux for 10 minutes, then 13.2 g. (0.045 mol) 3-(4-phenylacetamidopiperidino)-propyl chloride are added thereto. The reaction mixture is further heated under reflux for 6 hours, evaporated and then taken up in methylene chloride and washed with a dilute aqueous solution of sodium hydroxide. The organic phase is evaporated and the residue is triturated with diethyl ether. There are obtained 12.3 g. 2-[3-(4-phenylacetamidopiperidino)-propoxy]-benzonitrile (73% of theory); m.p. 105°–107° C.

EXAMPLE 2

The following compounds are obtained in a manner analogous to that described in Example 1:

| Product and starting materials | Yield % | m.p. °C. (solvent) |
|---|---|---|
| (a) methyl 2-[3-(4-benzamidopiperidino)-propoxy]-benzoate from methyl salicylate and 3-(4-benzamidopiperidino)-propyl chloride | 91 | 90–92 (cyclohexane) |
| (b) 2-[3-(4-benzamidopiperidino)-propoxy]-benzamide from salicylamide and 3-(4-benzamidopiperidino)-propyl chloride | 84 | 195–196 (ethanol) |
| (c) 2-[3-(4-benzamidopiperidino)-propoxy]-benzyl alcohol from saligenin and 3-(4-benzamidopiperidino)-propyl chloride | 61 | 130–131 (ethyl acetate) |
| (d) 2-[3-(4-cyclopropancarboxamido-piperidino)-propoxy]-benzonitrile from 2-hydroxybenzonitrile and 3-(4-cyclopropane-carboxamido-piperidino)-propyl chloride | 73 | 123–125 (diethyl ether) |
| (e) 2-[3-(4-benzamidopiperidino)-propoxy]-benzonitrile from 2-hydroxybenzonitrile and 3-(4-benzomidopiperidino)-propyl chloride | 67 | 143–145 (ethyl acetate |
| (f) 2-{3-[4-(4-fluorobenzamido)-piperidino]-propoxy}-benzonitrile from 2-hydroxybenzonitrile and 3-[4-(4-fluorobenzamido)-piperidino]-propyl chloride | 72 | 129–130 (dichloromethane) |
| (g) 2-{3-[4-(2-methylbenzamido)-piperidino]-propoxy}-benzonitrile from 2-hydroxybenzonitrile and 3-[4-(2-methylbenzamido)-piperidino]-propyl chloride | 54 | 118–120 (diethyl ether) |
| (h) 3-[3-(4-benzamidopiperidino)-propoxy]-benzonitrile from 3-hydroxybenzonitrile and 3-(4-benzamidopiperidino)-propyl chloride | 91 | 133–136 (dichloromethane) |
| (i) 4-[3-(4-benzamidopiperidino)-propoxy]-benzonitrile from 4-hydroxybenzonitrile and 3-(4-benzamidopiperidino)-propyl chloride | 85 | 175–177 (dichloromethane) |

EXAMPLE 3

2-[3-(4-Cyclohexanecarboxamidopiperidino)-propoxy]-benzonitrile.

A mixture of 7.35 g. (0.035 mol) 4-cyclohexanecarboxamidopiperidine, 8.4 g. (0.035 mol) 2-(3-bromopropoxy)-benzonitrile, 13.9 ml. (0.1 mol) triethylamine and 125 ml. tetrahydrofuran is heated under reflux for 6 hours and subsequently poured into water, extracted with methylene chloride and the extract evaporated. There are obtained 12.4 g. (97% of theory) 2-[3-(4-cyclohexanecarboxamidopiperidino)-propoxy]-benzonitrile; m.p. 110°–112° C.

EXAMPLE 4

The following compounds are obtained in a manner analogous to that described in Example 3:

| Product and starting materials | Yield % | m.p. °C. (solvent) |
|---|---|---|
| (a) 2-[3-(4-hydroxymethylpiperidino) propoxy]-benzonitrile from 2-(3-bromopropoxy)-benzonitrile and 4-hydroxymethylpiperidine | 77 | oil |
| (b) 2-[3-(4-aminopiperidino)-propoxy]-benzonitrile from 2-(3-bromopropoxy)-benzonitrile and 4-aminopiperidine | 93 | oil |
| (c) 2-[3-(4-acetamidopiperidino)-propoxy]-benzonitrile from 2-(3-bromopropoxy)-benzonitrile and 4-acetamidopiperidine | 58 | 103–106 (diethyl ether) |
| (d) 2-[3-(4-isobutyramidopiperidino)-propoxy]-benzonitrile from 2-(3-bromopropoxy)-benzonitrile and 4-isobutyramidopiperidine | 93 | 103–104 (dichloromethane) |
| (e) 2-{3-[4-(2-Methoxybenzamido)-piperidino]-propoxy}-benzonitrile from 2-(3-bromopropoxy)-benzonitrile and 4-(2-methoxybenzamido)-piperidine | 88 | oil |
| (f) 2-{3-[4-(2-aminobenzamido)-piperidino]-propoxy}-benzonitrile from 2-(3-bromopropoxy)-benzonitrile and 4-(2-aminobenzamido)-piperidine | 99 | oil |
| (g) 2-[3-(4-phenoxymethylpiperidino)-propoxy]-benzonitrile from 2-(3-bromopropoxy)-benzonitrile and 4-phenoxymethylpiperidine | 90 | oil |

EXAMPLE 5

2-{3-[4-(2-Acetoxybenzamido)-piperidino]-propoxy}-benzonitrile.

8.4 g. Sodium bicarbonate are added to a solution of 11.6 g. (0.045 mol) 2-[3-(4-aminopiperidino)-propoxy]-benzonitrile (see Example 4b) in 100 ml. methylene chloride and a solution of 9.9 g. (0.05 mol) 2-acetylsalicyclic acid chloride added thereto. The reaction mixture is heated under reflux for 4 hours, then poured into water, extracted with methylene chloride and the extract evaporated. After triturating the evaporation residue with diethyl ether, there are obtained 17.0 g. 2-{3-[4-(2-acetoxybenzamido)-piperidino]-propoxy}-benzonitrile (90% of theory); m.p. 80°–82° C.

EXAMPLE 6

The following compounds are obtained in a manner analogous to that described in Example 5:

| Product and starting materials | Yield % | m.p. °C. (solvent) |
|---|---|---|
| (a) 2-[3-(4-cyclopropanecarboxamido-piperidino)-propoxy]-benzonitrile (cf. Example 2d) from 2-[3-(4-aminopiperidino)-propoxy]-benzonitrile and cyclopropanecarbonyl chloride | 41 | 123–125 (diethyl ether) |
| (b) 2-{3-[4-(2-nitrobenzamido)-piperidino]-propoxy}-benzonitrile from 2-[3-(4-aminopiperidino)-propoxy]-benzonitrile and 2-nitrobenzoyl chloride | 94 | 117–120 (dichloromethane) |
| (c) 2-[3-(4-benzoyloxymethylpiperidino)-propoxy]-benzonitrile from 2-[3-(4-hydroxymethylpiperidino)-propoxy]-benzonitrile (cf. Example 4a) and benzoyl chloride | 98 | oil |
| (d) 2-{3-[4-(thiophene-2-carboxamido)-piperidino]-propoxy}-benzonitrile from 2-[3-(4-aminopiperidino)-propoxy]-benzonitrile and thiophene-2-carbonyl chloride | 66 | 97–99 (diethyl ether) |

EXAMPLE 7

2-[3-(4-Benzamidopiperidino)-propoxy]-benzoic acid.

A mixture of 23.6 g. (0.06 mol) methyl 2-[3-(4-benzamidopiperidino)-propoxy]-benzoate (see Example 2a), 200 ml. ethanol and 200 ml. 1 N aqueous sodium hydroxide solution is heated under reflux for 1 hour, then evaporated and the evaporation residue dissolved in water and acidified with dilute hydrochloric acid. This is followed by extraction with a mixture of 9 parts by volume of methylene chloride and 1 part by volume of ethanol. The extract is evaporated and the residue obtained is taken up in acetone and the hydrochloride of the desired product is precipitated out by the addition of ethereal hydrochloric acid. There are obtained 14.5 g. (59% of theory) 2-[3-(4-benzamidopiperidino)-propoxy]-benzoic acid hydrochloride; m.p. 207°–208° C.

EXAMPLE 8

2-[3-(4-Benzamidopiperidino)-propoxy]-benzoic acid (1H-tetrazol-5-yl)-amide.

2.7 g. (0.017 mol) N-Carbonyldiimidazole are added to a solution of 5.7 g. (0.015 mol) 2-[3-(4-benzamidopiperidino)-propoxy]-benzoic acid (see Example 7) in 30 ml. N,N-dimethylformamide. The reaction mixture is stirred for 1 hour at 100° C., 1.7 g. (0.02 mol) anhydrous 5-aminotetrazole is added thereto and the reaction mixture is stirred for 3 hours at 100° C., poured into water and filtered. There are obtained 3.3 g. (49% of theory) 2-[3-(4-benzamidopiperidino)-propoxy]-benzoic acid (1H-tetrazol-5-yl)-amide; m.p. 259°–260° C., after recrystallization from ethanol.

EXAMPLE 9

5-{2-[3-(4-Benzamidopiperidino)-propoxy]-phenyl}-1H-tetrazole.

A mixture of 18.1 g. (0.05 mol) 2-[3-(4-benzamidopiperidino)-propoxy]-benzonitrile (see Example 2e), 7.0 g. acetic acid, 4.5 g. (0.07 mol) sodium azide and 75 ml. n-butanol is heated under reflux for 70 hours, then mixed with a further 1.0 g. sodium azide and 2.0 g. acetic acid, further heated under reflux for 48 hours and thereafter substantially evaporated and filtered. There are obtained 15.2 g. 5-{2-[3-(4-benzamidopiperidino)-propoxy]-phenyl}-1H-tetrazole acetate (m.p. 260°–262° C.), from which, by reaction with a dilute aqueous solution of sodium hydroxide, and acidification, there are obtained 10.6 g. (53% of theory) 5-{2-[3-(4-benzamidopiperidino)-propoxy]-phenyl}-1H-tetrazole; m.p. 275°–277° C., after recrystallization from ethanol.

From the above-mentioned compound, by neutralization with dilute sodium hydroxide solution and subsequent freeze drying, there can be obtained the corresponding sodium salt. The yield is quantitative; m.p. 266°–270° C. (amorphous).

EXAMPLE 10

The following compounds are obtained in a manner analogous to that described in Example 9:

| Product and starting materials | Yield % | m.p. °C. (solvent) |
|---|---|---|
| (a) 5-{2-[3-(4-acetamidopiperidino)-propoxy]-phenyl}-1H-tetrazole from 2-[3-(4-acetamidopiperidino)-propoxy]-benzonitrile (cf. Example 4 c) and sodium azide | 47 | 241–242 (dimethylformamide/diethyl ether) |
| (b) 5-{2-[3-(4-isobutyramido-piperidino)-propoxy]-phenyl}-1H-tetrazole from 2-[3-(4-isobutyramidopiperidino)-propoxy]-benzonitrile (cf. Example 4 d) and sodium azide | 49 | 232–234 (dimethylformamide/diethyl ether) |
| (c) 5-{2-[3-(4-cyclopropanecarboxamido-piperidino)-propoxy]-phenyl}-1H-tetrazole from 2-[3-(4-cyclopropanecarboxamidopiperidino)-propoxy]-benzonitrile (cf. Example 2 d) and sodium azide | 45 | 244–246 (ethanol) |
| (d) 5-{2-[3-(4-phenylacetamido-piperidino)-propoxy]-phenyl}-1H-tetrazole from 2-[3-(4-phenylacetamidopiperidino)-propoxy]-benzonitrile (cf. Example 1) and sodium azide | 38 | 225–226 (isopropanol) |
| (e) 5-{2-[3-(4-cyclohexanecarboxamido-piperidino)-propoxy]-phenyl}-1H-tetrazole from 2-[3-(4-cyclohexanecarboxamidopiperidino)-propoxy]-benzonitrile (cf. Example 3) and sodium azide | 35 | 275–277 (dimethylformamide) |
| (f) 5-{2-{3-[4-(4-fluorobenzamido)-piperidino]-propoxy}-phenyl}-1H-tetrazole from 2-{3-[4-(4-fluorobenzamido)-piperidino]-propoxy}-benzonitrile (cf. Example 2 f) and sodium azide | 44 | 276–277 (isopropanol) |
| (g) 5-{2-{3-[4-(2-methylbenzamido)-piperidino]-propoxy}-phenyl}-1H-tetrazole from 2-{3-[4-(2-methylbenzamido)-piperidino]-propoxy}-benzonitrile (cf. Example 2 g) and sodium azide | 31 | 250–252 (ethyl acetate) |
| (h) 5-{2-{3-[4-(2-methoxybenzamido)-piperidino]-propoxy}-phenyl}-1H-tetrazole from 2-{3-[4-(2-methoxybenzamido)-piperidino]-propoxy}- | 39 | 194–196 (ethyl acetate) |

-continued

| Product and starting materials | Yield % | m.p. °C. (solvent) |
|---|---|---|
| benzonitrile (cf. Example 4 e) and sodium azide | | |
| (i) 5-{2-{3-[4-(2-hydroxybenzamido)-piperidino]-propoxy}-phenyl}-1H-tetrazole from 2-{3-[4-(2-acetoxy-benzamido)-piperidino]-propoxy}-benzonitrile (cf. Example 5) and sodium azide | 42 | 268–270 (dimethylformamide/diethyl ether) |
| (j) 5-{2-{3-[4-(2-aminobenzamido)-piperidino]-propoxy}-phenyl}-1H-tetrazole from 2-{3-[4-(2-aminobenzamido)-piperidino]-propoxy}-benzonitrile (cf. Example 4 f) and sodium azide | 27 | 285–287 (dimethyl formamide/diethyl ether) |
| (k) 5-{2-{3-[4-(2-nitrobenzamido)-piperidino]-propoxy}-phenyl}-1H-tetrazole from 2-{3-[4-(2-nitrobenzamido)-piperidino]-propoxy}-benzonitrile (cf. Example 6 b) and sodium azide | 38 | 260–261 (dimethylformamide/diethyl ether) |
| (l) 5-{2-{3-[4-(thiophene-2-carboxamido)-piperidino]-propoxy}-phenyl}-1H-tetrazole from 2-{3-[4-(thiophene-2-carboxamido)-piperidino]-propoxy}-benzonitrile (cf. Example 6 d) and sodium azide | 48 | 264–266 (dimethylformamide) |
| (m) 5-{2-[3-(4-phenoxymethyl-piperidino)-propoxy]-phenyl}-1H-tetrazole from 2-[3-(4-phenoxymethylpiperidino)-propoxy]-benzonitrile (cf. Example 4 g) and sodium azide | 29 | 120–122 (ethanol) |
| (n) 5-{2-[3-(4-benzoyloxymethyl-piperidino)-propoxy]-phenyl}-1H-tetrazole from 2-[3-(4-benzoyloxymethylpiperidino)-propoxy]-benzonitrile (cf. Example 6 c) and sodium azide | | |
| (o) 5-{3-[3-(4-benzamidopiperidino)-propoxy]-phenyl}-1H-tetrazole from 3-[3-(4-benzamidopiperidino)-propoxy]-benzonitrile (cf. Example 2 h) and sodium azide | 54 | 260–262 (dimethylformamide) |
| (p) 5-{4-[3-(4-benzamidopiperidino)-propoxy]-phenyl}-1H-tetrazole from 4-[3-(4-benzamidopiperidino)-propoxy]-benzonitrile (cf. Example 2i) and sodium azide | 47 | 248–250 (dimethylformamide/diethyl ether) |

EXAMPLE 11

2-[3-(4-Benzamidopiperidino)-propoxy]-benzamidoxime hydrochloride.

A mixture of 25.0 g. (0.069 mol) 2-[3-(4-benzamidopiperidino)-propoxy]-benzonitrile (see Example 2e), 15.9 g. (0.15 mol) sodium carbonate, 20.7 g. (0.30 mol) hydroxylamine hydrochloride, 125 ml. ethanol and 175 ml. water is stirred for 8 hours at 80° C., then poured into water, stirred with ethyl acetate and filtered. As residue, there are obtained 20.4 g. (68% of theory) 2-[3-(4-benzamidopiperidino)-propoxy]-benzamidoxime hydrochloride; m.p. 193°–194° C.

EXAMPLE 12

2-[3-(4-Benzamidopiperidino)-propoxy]-benzamidine hydrochloride.

A mixture of 38.0 g. (0.088 mol) 2-[3-(4-benzamidopiperidino)-propoxy]-benzamidoxime hydrochloride (see Example 11), 500 ml. ethanol and 20 ml. Raney nickel is hydrogenated for 6 hours at 70° C. and 30 bar hydrogen pressure. After filtering, the filtrate is evaporated and the residue is chromatographed on a column of silica gel (elution agent: methylene chloride/methanol) and the second fraction is evaporated. There are obtained 16.2 g. (44% of theory) 2-[3-(4-benzamidopiperidino)-propoxy]-benzamidine hydrochloride; m.p. 212°–215° C.

EXAMPLE 13

Ethyl 2-{2-[3-(4-benzamidopiperidino)-propoxy]-phenyl}-4-hydroxypyrimidine-5-carboxylate hydrochloride.

A mixture of 7.6 g. (0.018 mol) 2-[3-(4-benzamidopiperidino)-propoxy]-benzamide hydrochloride (see Example 12), 4.3 g. diethyl ethoxymethylenemalonate and 100 ml. ethanol is heated under reflux for 2 hours, evaporated and the residue recrystallized from ethanol. There are obtained 6.9 g. (70% of theory) ethyl 2-{2-[3-(4-benzamidopiperidino)-propoxy]-phenyl}-4-hydroxypyrimidine-5-carboxylate hydrochloride; m.p. 250°–252° C.

EXAMPLE 14

2-{2-[3-(4-Benzamidopiperidino)-propoxy]-phenyl}-4-hydroxypyrimidine-5-carboxylic acid.

In a manner analogous to that described in Example 7, by the alkaline saponification of ethyl 2-{2-[3-(4-benzamidopiperidino)-propoxy]-phenyl}-4-hydroxypyrimidine-5-carboxylate hydrochloride and subsequent neutralization, there is obtained 2-{2-[3-(4-benzamidopiperidino)-propoxy]-phenyl}-4-hydroxypyrimidine-5-carboxylic acid in a yield of 66% of theory; m.p. 145°–146° C. after recrystallization from ethanol.

EXAMPLE 15

Tablets containing active material.

| | for 1 tablet | for 100,000 tablets |
|---|---|---|
| I. active material = 5-{2-[3-(4-benzamidopiperidino)-propoxy]-phenyl}-1H-tetrazole | 10.000 mg. | 1.000 kg. |
| lactose | 67.000 mg. | 6.700 kg. |
| corn starch | 35.000 mg. | 3.500 kg. |
| II. polyvinylpyrrolidone (M.W. 30,000) | 3.000 mg. | 0.300 kg. |
| III. sodium carboxymethyl-amylopectin | 4.000 mg. | 0.400 kg. |
| cellulose powder | 20.000 mg. | 2.000 kg. |
| magnesium stearate | 1.000 mg. | 0.100 kg. |
| | 140.000 mg. | 14.000 kg. |
| water for granulation | | 1.000 kg. |

Production: The substances I are granulated with an aqueous solution of II, dried and sieved. The granulate is mixed with the substances III to give a tabletting mass. Tabletting is carried out to give 140 mg. tablets of 7 mm. diameter.

Experimental protocol.

Method

The experimental procedure for the measurement of bronchospasm is in principal that according to Konzett and Rössler (Versuchsanordnung zu Untersuchungen an der Bronchialmuskulatur, Naunyn-Schmiedebergs Arch. exp. Path. Pharmak., 195, 71–74/1940), as modified by Collier et al. (The bronchoconstrictor action of bradykinin in the guinea pig, Brit. J. Pharmacol., 15, 290/1960). In animals narcotized with 40 mg. sodium pentobarbital/kg. body weight, a Y cannula is introduced into the trachea and a venous cannula is introduced in the jugular vein. A cannula introduced in the carotid artery leads to a measurement chamber (Statham, P 23 Db), with which the arterial pressure is recorded via a direct-current voltage potential measuring bridge. Using a respiratory pump, rats are given an air volume, depending upon the size of the animal, of 1 to 2 ml. 64 times and guinea pigs of 7 to 15 ml. 72 times per minute. Narcosis must be so deep that spontaneous counter-respiration does not occur. Upon the appearance of a bronchospasm, initiated by the intravenous administration of the antigen, in the case of the respiratory volume remaining the same, all of the supplied volume of air can no longer flow into the lungs and part of it flows off through a side arm via a valve. The method developed by the firm Basile differs from the method originally described by Konzett and Rossler in that this air volume is measured indirectly via the rate of flow with the help of a thermoelement. The strength of a bronchospasm can then be recorded as a percentage reduction of the available bronchial volume. The theoretically maximum possible bronchospasm is obtained by closing the respiration tube on the animal so that all of the air supplied flows off through the valve.

Every 30 seconds, the valve is closed for 8 seconds by a relay and the total volume is pumped into the lungs in order again to expand the bronchi and alveoli and thus to make possible a sufficient gas exchange. The percentage decrease of the available bronchial volume (X) is calculated according to the following equation:

$$X = \frac{b-a}{m-a} \times 100$$

wherein a is the amplitude of the recorder in mm. at the commencement of the experiment, b is the height of the amplitude in mm. at a definite point of time and m is the maximum amplitude in mm. after closing the respiration tube on the animal.

Preparation of the antiserum.

The antigen is 2×crystallized ovalbumin. Equal amounts of a solution of the antigen in physiological sodium chloride solution and complete Freund's adjuvant are emulsified and injected intramuscularly in an amount of 2×0.15 ml. to male guinea pigs. The animals are bled and the pooled serum is stored at −20° C. For passive sensitization, guinea pigs are injected with 0.5 ml. of the antiserum diluted 1:50, 24 to 48 hours before initiation of the bronchospasm (see Davies and Johnson, Int. Arch. Allergy, 41, 648–654/1971).

The compounds according to the present invention are administered intravenously 5 minutes before administration of the antigen. The inhibition of bronchspasm (Br Sp) in % is determined 3 minutes after administration of the antigen, in comparison with a control group. The results obtained are given in the following Table:

TABLE

| compound of Example No. | dosage mg/kg. i.v. | % inhibition Br Sp % |
|---|---|---|
| 7 | 1.5 | 45 |
| 9 | 0.1 | 56 |
| 2a | 3.0 | 71 |
| 2b | 0.38 | 67 |
| 10g | 0.75 | 71 |
| aminophylline* | 24 | 29 |

*aminophylline = 2 mols theophylline + 1 mol ethylenediamine

The foregoing compounds can be used as such or they can be converted to salts with pharmacologically acceptable acids. They can be administered orally, as pills, tablets, capsules, powders and the like. The preferred form of oral administration is a tablet containing 10 to 300 mg of active compound, which nearly complies with the typical daily dosage. A preferred dosage is 30 to 100 mg.

The compounds can also be administered parenterally. Injection solutions containing 0.05 to 50 mg/ml of injection solution are administered.

It will be appreciated that the instant specification and examples are set forth by way of illustration and not limitation, and that various modifications and changes may be made without departing from the spirit and scope of the present invention.

We claim:

1. An N-phenoxyalkylpiperidine derivative of the formula

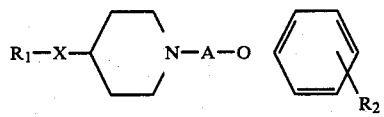

wherein
$R_1$ is a hydrogen atom or a $C_1$–$C_7$ alkanoyl radical, a trifluoroacetyl radical, a phenacetyl radical a $C_3$–$C_7$ cycloalkylcarbonyl radical, a furancarbonyl, thiophencarbonyl or pyridinecarbonyl radical, or a benzoyl radical which may be substituted by halogen, hydroxyl, $C_1$–$C_6$ alkyl, $C_1$–$C_6$ alkoxy, $C_1$–$C_6$ alkoxycarbonyl, acetyloxy, carboxyl, nitro, amino, nitrile, trifluoromethyl, carbamoyl, methylmercapto, methylsulfinyl, methylsulfonyl, acetyl, benzoyl, acetylamino, hydroxymethyl or $C_1$–$C_6$ alkoxy $C_1$–$C_6$ alkyl,
$R_2$ is a 1H tetrazol-5-yl radical,
X is an imino group, and
A is an alkylene radical containing 2 to 4 carbon atoms,
or a pharmacologically acceptable salt thereof.

2. A compound according to claim 1, wherein such compound is 5-{2-[3-(4-benzamidopiperidino)-propoxy]-phenyl}-1H-tetrazole or a pharmacologically acceptable salt thereof.

3. A compound according to claim 1, wherein such compound is 5-{2-{3-[4-(2-methylbenzamido)-piperidino]-propoxy}-phenyl}-1H-tetrazole or a pharmacologically acceptable salt thereof.

4. An anti-histaminic, anti-oedematous and anti-phlogistic composition of matter comprising an anti-histaminically, anti-oedematally or anti-phlogistically effective amount of a compound or salt according to claim 1 in admixture with a pharmacologically acceptable diluent.

5. A method of preventing or treating a histaminic, oedematous or phlogistic reaction in a patient comprising administering to such patient an anti-histaminically, anti-oedematally or anti-phlogistically effective amount of a compound or salt according to claim 1.

6. The method according to claim 5, wherein such compound is 5-{2-[3-(4-benzamidopiperidino)-propoxy]-phenyl}-1H-tetrazole, or 5-{2-{3-[4-(2-methylbenzamido)-piperidino]-propoxy}-phenyl}-1H-tetrazole, or a pharmacologically acceptable salt thereof.

* * * * *

UNITED STATES PATENT AND TRADEMARK OFFICE
CERTIFICATE OF CORRECTION

PATENT NO. : 4,348,401
DATED : September 7, 1982
INVENTOR(S) : Walter-Gunar Friebe et al It is certified that error appears in the above—identified patent and that said Letters Patent is hereby corrected as shown below:

Col. 4, line 37        Delete "cids" and insert --acids--

Col. 5(e)              (last line) delete "benzomidopiper-
                       idino" and insert --benzamido-
                       piperidino--

Signed and Sealed this

Twenty-eighth Day of December 1982

[SEAL]

Attest:

GERALD J. MOSSINGHOFF

Attesting Officer    Commissioner of Patents and Trademarks